United States Patent
Hansen et al.

(10) Patent No.: US 6,668,830 B1
(45) Date of Patent: Dec. 30, 2003

(54) LOW NOISE EXHALATION PORT FOR A RESPIRATORY MASK

(75) Inventors: Gary L. Hansen, Eden Prairie, MN (US); Christine Gale Kronich, St. Paul, MN (US); Clifford Thomas Jue, Santa Cruz, CA (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/443,504

(22) Filed: Nov. 19, 1999

(51) Int. Cl.$^7$ ............................................... A62B 18/02
(52) U.S. Cl. ............................ 128/206.21; 128/207.12
(58) Field of Search ...................... 128/200.24, 207.12, 128/207.16, 205.25, 207.13, 201.25, 205.27, 206.19, 206.15, 205.24, 206.29, 206.21; 126/299; 122/235.11

(56) References Cited

U.S. PATENT DOCUMENTS

| | | | | |
|---|---|---|---|---|
| 2,238,492 A | * | 4/1941 | Leguillon | 128/206.28 |
| 2,835,250 A | * | 5/1958 | Austin | 128/201.15 |
| 3,643,686 A | * | 2/1972 | Koegel | 137/512 |
| 4,192,301 A | * | 3/1980 | Hardwick | 128/205.17 |
| 4,770,169 A | * | 9/1988 | Schmoegner et al. | 128/207.13 |
| 4,944,310 A | * | 7/1990 | Sullivan | 128/848 |
| 4,945,906 A | * | 8/1990 | Lindkvist | 128/203.29 |
| 4,974,586 A | * | 12/1990 | Wandel et al. | 128/206.28 |
| 5,042,478 A | * | 8/1991 | Kopala et al. | 128/207.18 |
| 5,117,819 A | * | 6/1992 | Servidio et al. | 128/204.18 |
| 5,174,113 A | * | 12/1992 | Deville | 60/309 |
| 5,271,391 A | * | 12/1993 | Graves | 128/207.18 |
| 5,400,781 A | * | 3/1995 | Davenport | 128/206.28 |
| 5,419,317 A | * | 5/1995 | Blasdell et al. | 128/205.19 |
| 5,477,852 A | * | 12/1995 | Landis et al. | 128/207.18 |
| RE35,339 E | | 10/1996 | Rapoport | |
| 5,657,752 A | * | 8/1997 | Landis et al. | 128/207.13 |
| 5,921,239 A | * | 7/1999 | McCall et al. | 128/205.25 |
| 5,937,851 A | * | 8/1999 | Serowski et al. | 128/202.27 |
| 6,006,748 A | * | 12/1999 | Hollis | 128/205.24 |
| 6,102,034 A | * | 8/2000 | Buhlmann | 128/201.29 |
| 6,192,886 B1 | * | 2/2001 | Rudolph | 128/207.13 |
| 6,412,485 B1 | * | 7/2002 | Saieva | 128/205.24 |
| 6,412,487 B1 | * | 7/2002 | Gunaratnam et al. | 128/206.24 |
| 6,418,928 B1 | * | 7/2002 | Bordewick et al. | 128/205.25 |
| 6,435,181 B1 | * | 8/2002 | Jones et al. | 128/204.18 |
| 6,467,483 B1 | * | 10/2002 | Kopacko et al. | 128/207.12 |

FOREIGN PATENT DOCUMENTS

| WO | 94/02190 | * | 2/1994 |
|---|---|---|---|
| WO | 98/34665 | * | 8/1998 |

* cited by examiner

Primary Examiner—Weilun Lo
Assistant Examiner—Teena Mitchell
(74) Attorney, Agent, or Firm—Rothwell, Figg, Ernst & Manbeck, PC

(57) ABSTRACT

A low noise exhalation port for a respiratory mask has a body including a proximal end operably connected to an internal area of the mask to vent carbon dioxide exhaled by a person from the mask, and a distal end. The venting device vents a gas out of the respiratory mask so as to substantially reduce inhalation by the person of the exhaled carbon dioxide. An exit passage portion is provided at the distal end and extends partially through the body and communicates with an exterior of the mask, the exit passage portion having a substantially regular cross-sectional area. An entrance passage portion is provided at the proximal end and extends partially through the body, the entrance passage portion communicating with an interior of the mask and further communicating with the exit passage portion, the entrance passage portion decreasing in cross-sectional area from the interior of the mask to the exit passage portion.

20 Claims, 2 Drawing Sheets

LOW NOISE EXHALATION PORT FOR A RESPIRATORY MASK

BACKGROUND OF THE INVENTION

1. Field of the Invention

The present invention relates generally to the field of respiratory masks.

2. Description of the Background Art

A respiratory mask is a device used to deliver a gas or gases to a person. The mask shell is fitted over a face of the person in order to supply a gas to a respiratory system of the person. A related art respiratory mask generally includes a mask shell, a gas supply hose, and a vent aperture. The related art vent aperture is typically a simple hole in the mask shell that allows gas to escape the related art mask shell. Exhaled air is flushed out of the related art respiratory mask by the positive pressure generated by the gas supply hose. This is taught by Rapaport U.S. Pat. No. Re. 35,339.

The related art respiratory mask may be used to deliver any variety of gases, including air or oxygen, and a variety of medicines or treatments. A strap or other attaching means (not shown) may be affixed to the related art mask shell and may be fitted over the head of the person. Constant pressure gas is therefore delivered, with the related art vent aperture maintaining a substantially constant pressure in the mask. This is referred to as a continuous positive airway pressure (CPAP) mask. The related art vent aperture allows the patient to exhale without accumulating excessive carbon dioxide in the mask.

Several drawbacks exist with the venting aperture of the related art respiratory mask. First, the air circulation within the mask shell and vent aperture may create annoying noises. The related art aperture may create a noisy, turbulent airflow. Second, a jet of air from the vent aperture may impinge on the wearer or on nearby persons. The vent aperture and a resulting air jet are relatively close to the face of the wearer, and will in all likelihood be in the region of persons near to or conversing with the wearer. As a result, these drawbacks may affect compliance with a gas therapy.

Therefore, there remains a need in the art for an improved respiratory mask.

SUMMARY OF THE INVENTION

In accordance with the present invention, a low noise exhalation port for a respiratory mask comprises a venting device having a body including a proximal end operably connected to an internal area of said mask to vent carbon dioxide exhaled by a person from said mask, and a distal end, said venting device venting a gas out of said respiratory mask so as to substantially reduce inhalation by said person of the exhaled carbon dioxide. An exit passage portion is provided at said distal end and extending partially through said body and communicates with an exterior of said mask, said exit passage portion having a substantially regular cross-sectional area. An entrance passage portion is provided at said proximal end and extends partially through said body, said entrance passage portion communicating with an interior of said mask and further communicating with said exit passage portion, said entrance passage portion decreasing in cross-sectional area from said interior of said mask to said exit passage portion.

DETAILED DESCRIPTION OF THE PREFERRED EMBODIMENTS

Figure 1:
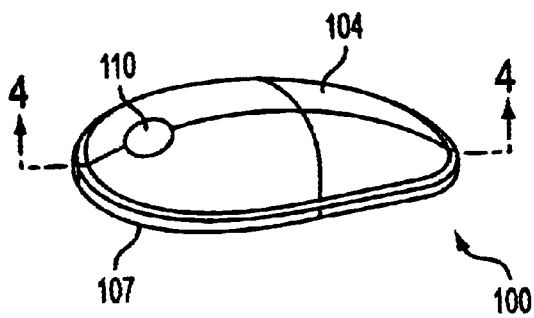
FIG. 1 is a perspective view, partly schematic, showing a low noise exhalation port for a respiratory mask in accordance with the invention.

FIG. 1 shows a low noise exhalation port 100 for a respiratory mask. The exhalation port 100 includes a body 104, a circumference 107, and a port opening 110. The outer surface of the body 104 is preferably convex in shape. The exhalation port 100 is adapted to fit into a corresponding hole in a respiratory mask (not shown).

Figure 2:
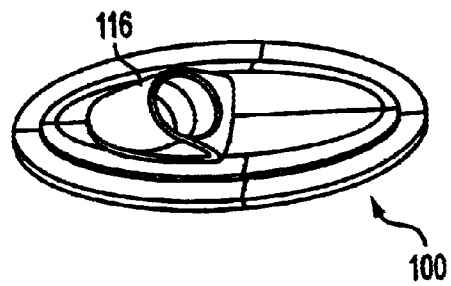
FIG. 2 is a perspective view, partly schematic, showing an underside of the exhalation port of FIG. 1.

FIG. 2 shows an underside of the exhalation port 100, showing a port wall 116 extending from the exterior of the port opening 110. The port wall 116 is preferably substantially circular in cross-section, although other shapes such as ovoid or rectangular may be used, for example. It can be seen that the port wall 116 is angled in relation to the plane of the circumference 107.

Figure 3:
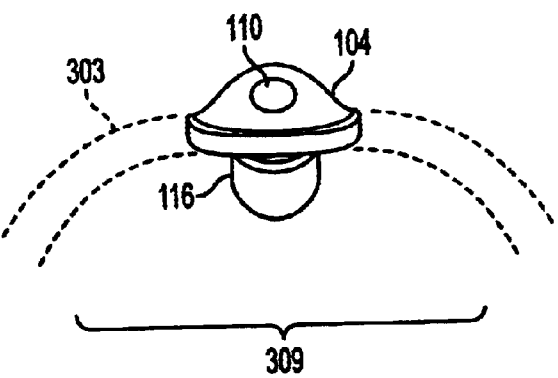
FIG. 3 is a perspective view, partly schematic, showing the exhalation port of FIG. 1 mounted into a mask shell.

FIG. 3 shows the exhalation port 100 mounted into a mask shell 303. The port wall 116 extends into the interior region 309 of the mask shell 303, while the port opening 110 communicates with the exterior of the mask shell 303.

Figure 4:
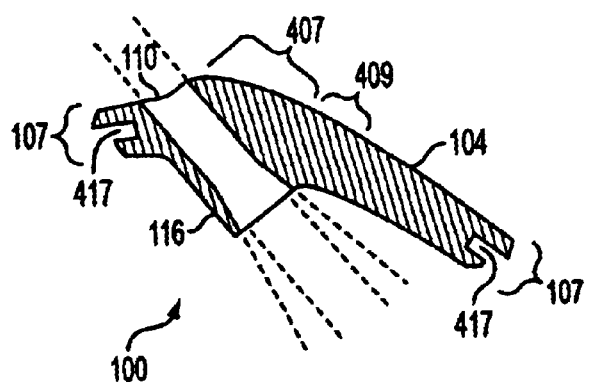
FIG. 4 is a cross-sectional view, showing a cross-section AA of the exhalation port of FIG. 1.

FIG. 4 shows a cross-section AA of the exhalation port 100. It can be seen that the port opening 110 may have two regions: an exit passage portion 407 having a substantially regular cross-sectional area terminating in an exit aperture, and an entrance passage portion 409 that decreases in cross-sectional area from the interior region 309 of the mask to the exit passage portion 407. In a preferred embodiment, the exit passage portion 407 is substantially circular and the entrance passage portion 409 is substantially conical in shape.

Also shown in FIG. 4 is the circumference 107, including a circumferential groove 417. The circumferential groove 417 allows the exhalation port 100 to be removably inserted into the corresponding opening in the respiratory mask (not shown).

Figure 5:
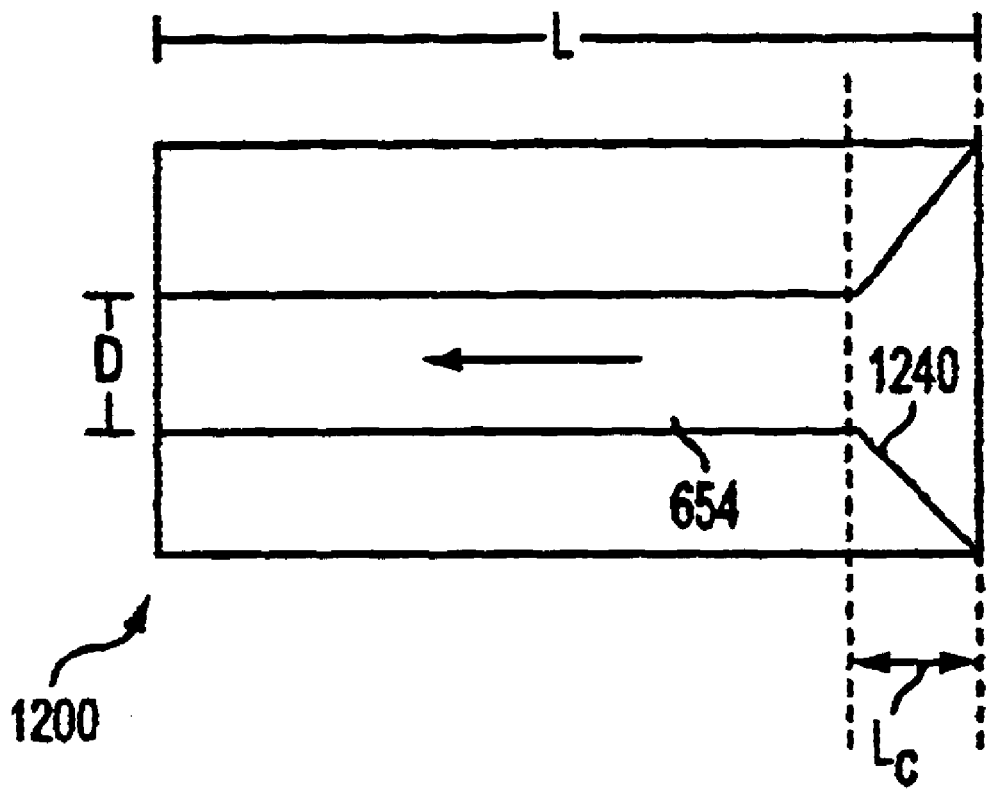
FIGS. 5 is a schematic cross-section showing entrance and exit passage geometries, along with entrance and exit ends, in accordance with the invention.

FIG. 5 shows preferred entrance and exit passage geometries, along with shapes of entrance and exit ends. The airflow is depicted by an arrow.

FIG. 5 shows an embodiment 1200 wherein the interior passage 654 has a flare 1240 at the interior end of the port. This preferred embodiment has a cone-shaped entrance region which enhances laminar flow within the vent passageway. This preferred embodiment has a cylindrically-shaped exit region, most preferably without any outward flare or bevel, to avoid standing wave production which is associated with noise.

In particularly preferred embodiments, with reference to FIG. 5, the port has an overall port length L that is substantially greater than the exit aperture diameter D. In preferred embodiments, the ratio of the overall port length to the diameter of the port at the exit thereof is at least about 2:1 or greater. Also, in preferred embodiments, the longitudinal length of the cone-shaped entrance region C represents about 10–80% of the overall longitudinal port length L, most preferably about 30–35%.

In preferred embodiments, the venting device of the present invention maintains a gas flow volume of at least about 10, most preferably about 15 liters per minute at a continuous positive airway pressure of about 3–4 cm $H_2O$.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A low noise exhalation port for a respiratory mask, said exhalation port comprising:
   a venting device having a body including a proximal end and a distal end, said body adapted to a fit in a hole in a respiratory mask such that said proximal end is oriented toward the face of a wearer and said distal end is oriented away from the wearer's face;
      an exit passage portion at said distal end and extending partially through said body, said exit passage portion having a substantially cylindrical portion with a substantially regular cross-sectional area; and
      an entrance passage portion at said proximal end and extending partially through said body, said entrance passage portion communicating with said exit passage portion, said entrance passage portion decreasing in cross-sectional area from said proximal end to said exit passage portion, said entrance portion being substantially conical.

2. The port of claim 1 having and exit aperture, and having an overall port length that is substantially greater than an exit aperture diameter.

3. The port of claim 2 wherein said overall port length and said exit aperture diameter are at a ratio of at least about 2:1.

4. The port of claim 1 wherein said venting device maintains a gas flow volume of at least about 10 liter per minute at a continuous positive airway pressure of about 3–4 cm H2O.

5. The port of claim 1 wherein said venting device maintains a gas flow volume of about 15 liters per minute at a continuous positive airway pressure of about 3–4 cm H2O.

6. The port of claim 1, wherein said exhalation port is formed of an elastomeric material.

7. The port of claim 1, wherein said body is configured to fit in an opening in a continuous positive airway pressure mask.

8. The port of claim 1, wherein said body has a circumferential groove adapted to fit into an opening in a respiratory mask.

9. The port of claim 8 wherein said entrance and exit passage portions are defined by a port wall oriented at an angle relative to a plane of said circumferential groove.

10. The port of claim 1, wherein said exhalation port is adapted to be removably inserted into a respiratory mask.

11. The port of claim 1 wherein the conical entrance portion has a longitudinal length that represents about 10–80% of an overall longitudinal port length of said port.

12. The port of claim 11, wherein the longitudinal length of the conical entrance portion represents about 30–35% of the overall port length.

13. A respiratory mask comprising
   a mask shell having an interior for orientation toward the face of a patient and an exterior for orientation away from the face of a patient; and
   an exhalation port including a body defining a passage through said mask shell, said passage including an exit passage portion having a substantially cylindrical portion with a substantially regular cross-sectional area terminating at an exit aperture on an exterior of said mask and a substantially conical entrance passage portion that decreases in cross-sectional area from an interior of said mask to said exit passage portion.

14. A respiratory mask according to claim 13, wherein an opening is formed through said mask shell and said body is disposed within said opening.

15. A respiratory mask according to claim 14, wherein said body includes a circumferential groove engaging edges of said opening.

16. A respiratory mask according to claim 13, wherein said exit passage portion of said exhalation port is substantially cylindrical in shape.

17. A method of providing continuous positive airway pressure therapy to a patient comprising the steps of
   positioning a respiratory mask on the face of the patient such that an interior of the respiratory mask is oriented toward the patient's face and an exterior of the respiratory mask is oriented away from the patient's face;
   providing continuous positive airway pressure to the patient via the respiratory mask; and
   venting exhalation gases from the respiratory mask via an exhaust port defining a passage through the respiratory mask having a substantially conical entrance portion of decreasing cross-sectional area in a direction away from the patient's face and a substantially cylindrical exit passage portion of substantially regular cross-sectional area extending from the entrance portion to an exterior of the respiratory mask.

18. A low noise exhalation port for a respiratory mask, said exhalation port comprising:
   a venting device having a body including a proximal end and a distal end, said body adapted to a fit in a hole in a respiratory mask such that said proximal end is oriented toward the face of a wearer and said distal end is oriented away from the wearer's face;
   an exit passage portion at said distal end and extending partially through said body, said exit passage portion having a substantially cylindrical portion with a substantially regular cross-sectional area without an outward flare at said distal end; and
   an entrance passage portion at said proximal end and extending partially through said body, said entrance passage portion communicating with said exit passage portion, said entrance passage portion decreasing in cross-sectional area from said proximal end to said exit passage portion.

19. A respiratory mask comprising
   a mask shell having an interior for orientation toward the face of a patient and an exterior for orientation away from the face of a patient; and
   an exhalation port including a body defining a passage through said mask shell including a proximal end and a distal end, said body oriented in said mask such that said proximal end is oriented toward the face of a wearer and said distal end is oriented away from the wearer's face, said passage including an exit passage portion having a substantially cylindrical portion with a substantially regular cross-sectional area without an outward flare at said distal end terminating at an exit aperture on an exterior of said mask and an entrance passage portion that decreases in cross-sectional area from an interior of said mask to said exit passage portion.

20. A method of providing continuous positive airway pressure therapy to a patient comprising the steps of positioning a respiratory mask on the face of the patient such that an interior of the respiratory mask is oriented toward the patient's face and an exterior of the respiratory mask is oriented away from the patient's face;

providing continuous positive airway pressure to the patient via the respiratory mask; and venting exhalation gases from the respiratory mask via an exhaust port including a proximal end and a distal end, said exhaust port oriented in said mask such that said proximal end is oriented toward the face of a wearer and said distal end is oriented away from the wearer's face, said exhaust port defining a passage through the respiratory mask having a entrance portion of decreasing cross-sectional area in a direction away from the patient's face and a substantially cylindrical exit passage portion of substantially regular cross-sectional area extending from the entrance portion to an exterior of the respiratory mask, without having an outward flare at said distal end.

* * * * *